(12) United States Patent
Egle

(10) Patent No.: US 7,118,526 B2
(45) Date of Patent: Oct. 10, 2006

(54) DEVICE FOR GENERATING AN ARTIFICIAL CONSTRICTION IN THE GASTROINTESTINAL TRACT

(75) Inventor: Walter Egle, Koblach (AT)

(73) Assignee: AMI Agency for Medical Innovatons GmbH, Götzis (AT)

( * ) Notice: Subject to any disclaimer, the term of this patent is extended or adjusted under 35 U.S.C. 154(b) by 329 days.

(21) Appl. No.: 10/857,939

(22) Filed: Jun. 2, 2004

(65) Prior Publication Data
US 2005/0283041 A1  Dec. 22, 2005

(30) Foreign Application Priority Data
Jun. 4, 2003  (AT)  ............... A 862/2003

(51) Int. Cl.
*A61F 2/00* (2006.01)
*A61B 17/00* (2006.01)
(52) U.S. Cl. .................. 600/37; 606/151; 600/31
(58) Field of Classification Search ........... 600/37–41, 600/29–31; 128/897–899, DIG. 25; 606/151–158, 606/201–203
See application file for complete search history.

(56) References Cited

U.S. PATENT DOCUMENTS

| 4,592,339 A | 6/1986 | Kuzmak et al. |
| 6,470,892 B1 | 10/2002 | Forsell |
| 6,511,490 B1 | 1/2003 | Robert |
| 2002/0198548 A1 | 12/2002 | Robert |

FOREIGN PATENT DOCUMENTS

| EP | 0 702 529 | 3/1996 |
| EP | 1 389 453 | 2/2004 |
| WO | 03/020183 | 3/2003 |
| WO | 2004/019671 | 3/2004 |

*Primary Examiner*—John P. Lacyk
(74) *Attorney, Agent, or Firm*—Wenderoth, Lind & Ponack, L.L.P.

(57) ABSTRACT

A device for generating an artificial constriction in the gastrointestinal tract comprises a band (1), which can be placed annularly about a particular portion of the gastrointestinal tract, and a closure device (2) for connecting the end regions of the band (1), placed annularly about the portion of the gastrointestinal tract, which, in the closed state of the closure device (2) encompasses a throughlet opening (6), the band (1) comprising a hollow chamber (14) fillable with a filling medium and extending at least over a large portion of the length of the band (1), and upon filling the hollow chamber (14) a wall (11), delimiting the throughlet opening (6) of the band (1), extends in the direction toward the axis (7) of the throughlet opening decreasing the size of the throughlet opening. The device comprises further a foamed material body (13), connected with the band (1), which adjoins the surface (12), facing away from the throughlet opening (6), of the wall (11) delimiting the throughlet opening. The foamed material body (13) is adhered to the wall (11) at least over a large portion, preferably over the entire area, of its area in contact with the wall (11).

14 Claims, 2 Drawing Sheets

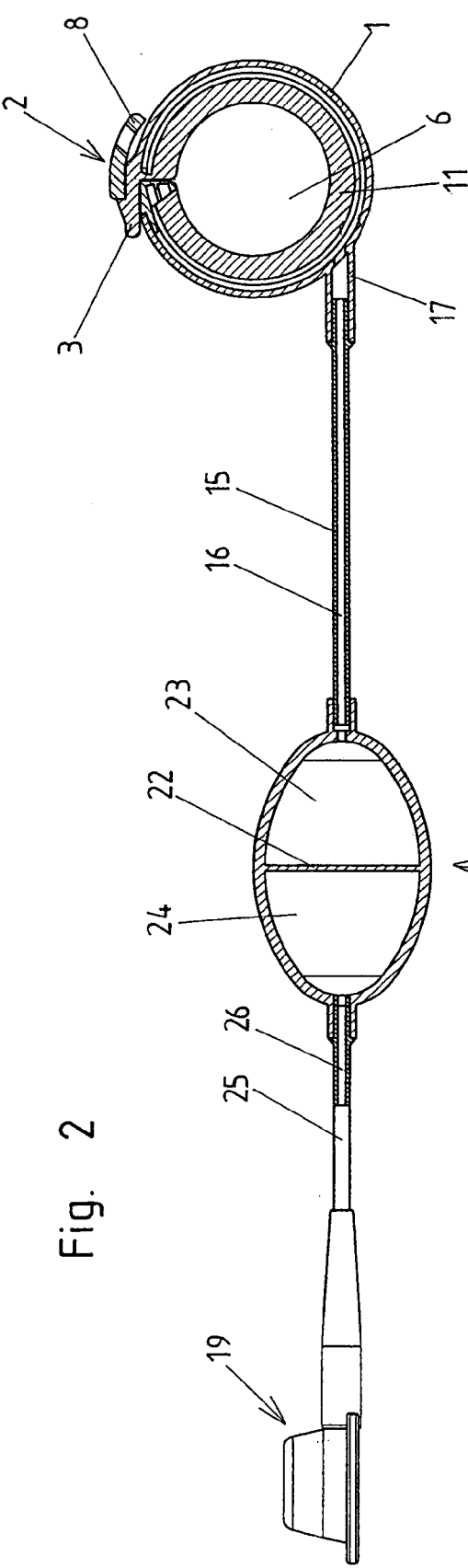
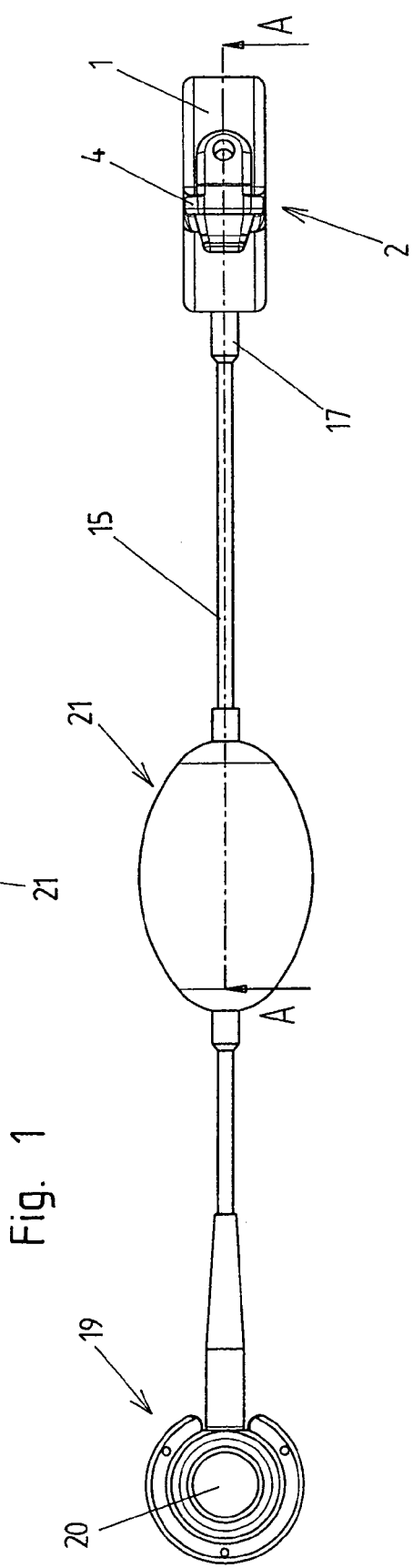

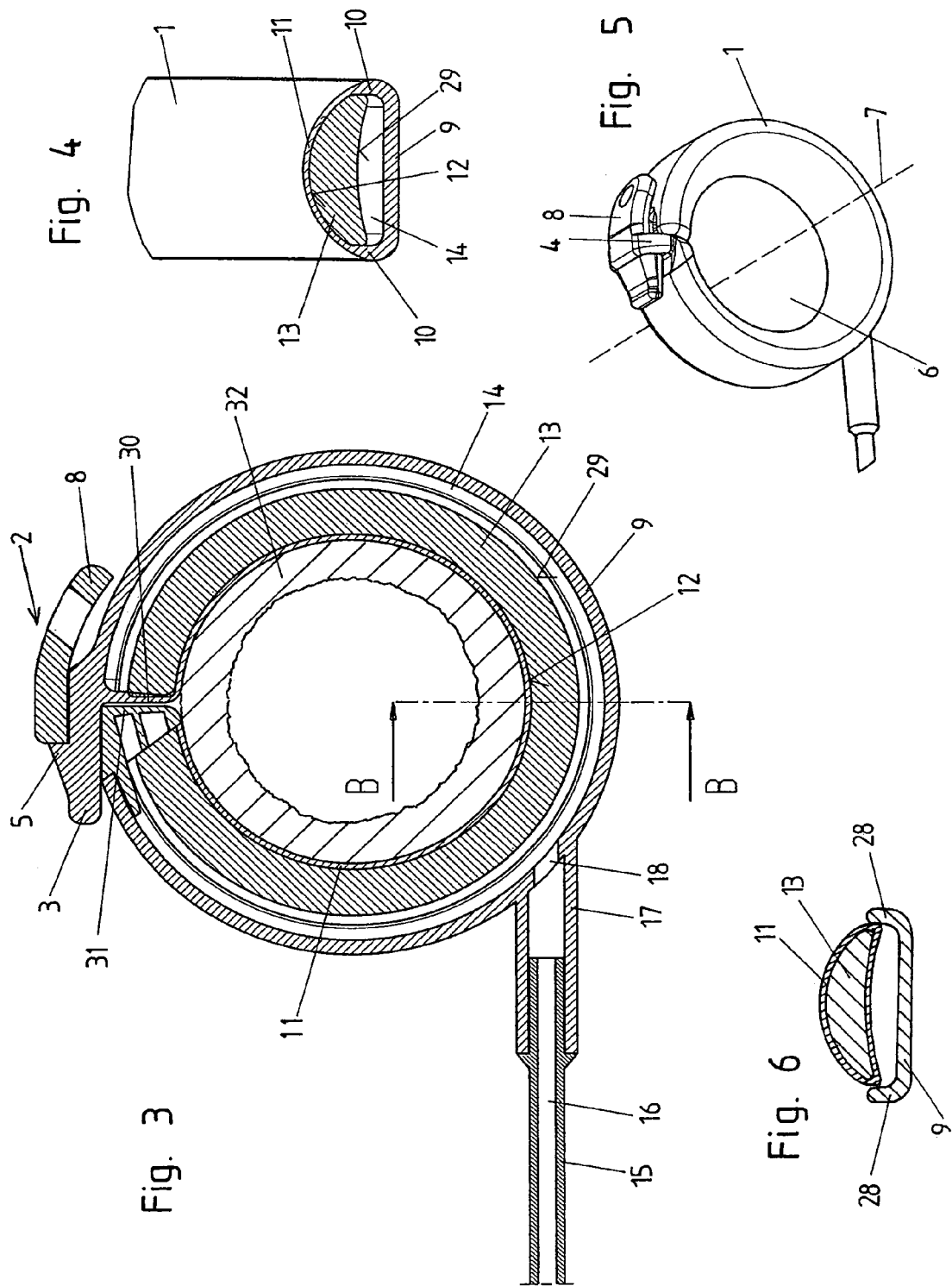

DEVICE FOR GENERATING AN ARTIFICIAL CONSTRICTION IN THE GASTROINTESTINAL TRACT

BACKGROUND OF THE INVENTION a) Field of the Invention

The invention relates to a device for generating an artificial constriction in the gastrointestinal tract with a band, which can be placed annularly about a particular portion of the gastrointestinal tract, and a closure device for connecting the end regions of the band placed annularly about the portion of the gastrointestinal tract, which, in the closed state of the closure device, encompasses a throughlet opening, the band having a hollow chamber fillable with a filling medium and extending at least over a large portion of the length of the band and, upon the filling of the hollow chamber, a wall of the band delimiting the throughlet opening extends in the direction toward the axis of the throughlet opening and decreasing the throughlet opening, and the device further comprising a foamed material body connected with the band.

b) Description of Related Prior Art

A device for generating an artificial constriction in the gastrointestinal tract is disclosed for example in EP 0 702 529 B1 in the form of a gastric band. This device comprises a band, which can be placed about the gastric inlet, developed with a longitudinally extending interior hollow chamber. To close this band placed annularly about the gastric inlet, it comprises a closure device with a first closure part disposed at one end of the band having an insertion opening, and a second closure part disposed at the other end of the band, which can be introduced through the insertion opening and which is latchable with respect to it. To constrict the passageway cross section of the throughlet opening of the band, and consequently of the gastric inlet, the hollow chamber of the band is filled with a filling medium, the quantity of the filling medium depending on the desired passageway cross section. To fill the band with the filling medium, an injection port, connected with the band is provided, which is implanted under the skin of the patient.

Apart from the development as a stomach band, a device of this type can in particular also be developed as an anal band for the closure of an, optionally, artificial anus.

A device of the above described type is disclosed in U.S. Pat. No. 6,511,490 B2. The device comprises a foamed material body encompassing the throughlet opening with a rough surface, which, for example, is an open cell polyurethane or silicone foam. This is said to prevent the device, placed about the stomach, from sliding. The foamed material body is disposed on the side face of the fillable band facing the throughlet opening.

U.S. Pat. No. 4,592,339 discloses a gastric band, which includes a multilayered band segment. Over a portion of the longitudinal extent of the band segment an inflatable balloon is disposed between the layers of this band segment, with which the size of the throughlet opening of the gastric band can be reduced.

A further gastric band is disclosed in WO 03/020183 A1. The throughlet opening of this gastric band can be varied in particular by means of a motor-driven setting unit, which cooperates with an end segment of the band. The band is encompassed by a layer of a viscoelastic material in order to protect the wall of the stomach. The viscoelastic material can comprise a foamed material.

One problem entailed in such devices for generating an artificial constriction in the gastrointestinal tract, which comprises a band with a fillable hollow chamber, is that these, sooner or later in the course of their use, can leak, such that their function is no longer ensured. Consequently, surgical removal and replacement of this band is required, which is tied to a corresponding strain on the patient. Such leaks in practice occur especially in the diaphragm delimiting the band toward the throughlet opening. Such leaks can occur for example due to material fatigue in the course of use or due to an overfilling of the band. For so-called "early" leaks, which occur up to approximately one year after the insertion of the band, most often injuries are responsible, which have occurred through a surgical instrument during the surgical, in particular laparoscopic, placement of the band.

AIM AND SUMMARY OF THE INVENTION

One important aim of the invention is providing an improved device of the type described in the introduction, in which the frequency of surgical interventions, necessitated by a leak of the band, is reduced.

This is attained according to the invention by a device for generating an artificial constriction in the gastrointestinal tract with a band that can be placed annularly about a particular portion of the gastrointestinal tract, and a closure device for connecting the end regions of the band placed annularly about the portion of the gastrointestinal tract, which, in the closed state of the closure device, encompasses a throughlet opening, the band comprising a hollow chamber fillable with a filling medium and extending at least over a large portion of the length of the band and, upon filling the hollow chamber, a wall of the band delimiting the throughlet opening extends in the direction toward the axis of the throughlet opening with the reduction of the throughlet opening, and a foamed material body, which adjoins the surface, facing away from the throughlet opening, of the wall delimiting the throughlet opening, the foamed material body being adhered to the wall at least over a large portion of its area in contact on the wall.

Due to the development according to the invention a significantly improved security against leakage can be attained, the imperviousness of the hollow chamber normally also being given even in the event of damage of the wall delimiting the throughlet opening.

In an advantageous embodiment of the invention the foamed material body is comprised of silicone foam.

As the filling medium can be employed, for example, sterile water. To further improve the leakage security, a fluid can also be used having a higher viscosity, for example silicone gel.

Further advantages and details of the invention will be explained in the following in conjunction with the enclosed drawing, on the basis of which additional aims of the invention are also evident.

BRIEF DESCRIPTION OF THE DRAWING

In the drawing depict:

FIG. 1 view of an embodiment example of the invention,

FIG. 2 side view, partially in section along line AA of FIG. 1,

FIG. 3 enlarged detail from FIG. 2,

FIG. 4 section along line BB of FIG. 3,

FIG. 5 perspective representation of the band with the closure device, and

FIG. 6 schematic representation of a modified embodiment in a section corresponding to FIG. 4.

DESCRIPTION OF THE PREFERRED EMBODIMENT EXAMPLES

The embodiment example depicted in the figures of a device according to the invention is developed as a gastric band and comprises a band 1 to be placed annularly about the corresponding portion 32, indicated only schematically in cross section in FIG. 3, of the gastrointestinal tract, in this case the stomach, the inlet to the stomach or the esophagus. In the proximity of its two ends the band is provided with parts of a closure device 2. The closure device comprises an extension 3 at one end of band 1 and a stay 4 disposed at the other end of the band with an insertion opening for putting through the extension 3. To close the closure device 2, the extension 3 is pulled through the insertion opening in stay 4, a catch lip 5 on extension 3 latches with the stay 4 securing the closure device against unintentional opening.

In the closed state of the closure device 2 the band 1, which is now annular, encompasses a throughlet opening 6.

The catch lip 5 preferably projects beyond the side, facing away from the throughlet opening 6, and the edge sides of the extension 3, facing in the direction of an axis 7 of the throughlet opening 6, the catch lip 5 having a shape broadening conically, viewed from the free end of extension 3, in order to permit pulling the extension through the insertion opening of stay 4. On the side, which in the inserted state extends behind the edge of the insertion opening of stay 4, the catch lip 5 is developed in the form of a step and projects approximately perpendicularly from extension 3.

The extension 3 with its catch lip 5 and the stay are preferably comprised of an elastic material, in particular silicone, with a hardness and, further, with a cooperating geometric shape, such that the closure device opens under a force-open tension exceeding a specified limit value. Thereby a safety closure can be provided, through which an impermissibly high pressure in the encompassed body organ can be avoided.

From stay 4 projects a pull tab 8 in the direction approximately opposite to the direction of insertion of extension 3, whereby by applying medical instruments on the pull tab, on the one hand, and, on the other hand, on the extension 3 guided with its front end through the insertion opening in stay 4, closing the closure device 2 is facilitated.

The parts of the closure device 2, disposed at both ends of the band 1, can be disposed on stoppers, which project into the ends of the band, are glued into these ends and close these ends. The integral development from a single piece of material of the closure device, or parts thereof, with the band 1, especially on the side of the extension 3, is conceivable and possible.

In the embodiment example depicted in FIG. 1 to 5, the band comprises a circumferentially closed tube with a back segment 9 facing away from the throughlet opening 6 and a wall (or skin or diaphragm) 11 located on the side of the throughlet opening 6 and delimiting the throughlet opening 6. The back segment 9 has a greater thickness than the wall 11, reducing its elastic extensibility. The back segment 9 can further also be provided with a reinforcement layer (not shown in the figures), which, for example, can be embedded into the material of the back segment 9 or it can be adhered onto the surface, facing away from the throughlet opening 6, of the back segment 9. Such a reinforcement layer can include filaments continuous in the longitudinal direction and advantageously also in the transverse direction, over its entire extent and can be developed in particular as a rectangular weave fabric, for example of a synthetic material.

Between the back segment 9 and the wall 11 are disposed connection segments 10, extending from the two edge sides of the back segment 9 in the direction toward the throughlet opening 6, whose material thickness is also greater that that of the wall 11. It is in principle conceivable and possible to omit these connection segments 10.

The surface 12, facing away from the throughlet opening 6, of wall 11 is adjoined by a foamed material body 13, which is preferably comprised of silicone foam. This foamed material body 13, which extends over the entire length of the wall 11 delimiting the throughlet opening 6, is adhered to the wall 11 at least over a large portion of its area in contact with the wall. The foamed material body 13 is preferably over the entire area fully adhered over the entire length of wall 11. Between the surface 29, facing away from the throughlet opening 6, of the foamed material body 13 and the back segment 9 extends a hollow chamber 14 at least over a large portion of the length of the band 1, preferably over the entire length of band 1. Consequently, the hollow chamber 14 on the side, facing the throughlet opening 6, is delimited by the foamed material body 13 and on its side remote from the throughlet opening 6, is delimited by the back segment 9. In the embodiment example depicted, it is delimited on the side by the connection segments 10. This lateral demarcation could also be accomplished by the foamed material body 13, which, for this purpose, could comprise for example appropriate lateral strip-like elevations oriented in the direction toward the back segment 9 or it could be developed, viewed from the hollow chamber 14, such that it is arched convexly. The hollow chamber 14 is delimited at its long-side ends by front-side walls 30, 31, which close the hollow chamber 14 at both ends of band 1.

The wall 11 and the foamed material body 13 are developed such that they are elastically extensible. The wall 11 is preferably comprised of a non-foamed (solid) silicone as are the back segment 9 and the optionally provided connection segments 10.

The device comprises furthermore a connection tubule 15, whose inner channel 16 communicates with the hollow chamber 14. For this purpose on band 1 in a central segment of the same a connecting piece 17 is disposed, which, for example, can be integrally developed with the back segment 9 of a single piece of material, the connecting piece 17 being connected via an opening 18 in the back segment 9 with the hollow chamber 14 and the connection tubule 15, projecting with a terminal segment into the connecting piece 17 is adhered in it. The other end of the connection tubule 15 is connected to a bulb 21, whose inner volume is divided into two chambers 23, 24 by an elastically extensible partition 22, and channel 16 of the connection tubule 15 communicates with chamber 23. To the bulb 21 is further connected a connection tubule 25, whose inner channel 26 communicates with chamber 24. The other end of this connection tubule 25 is connected to a conventional injection port 19.

Chamber 23 of bulb 21 is filled with silicone gel or another fluid well tolerated by the body, which has a higher viscosity than water. The hollow chamber 14 of band 1 and the connection tubule 15 are prefilled with this filling medium. The chamber 24 of the bulb 21 is prefilled with a pressure medium, for example sterile water.

After the band 1 has been surgically placed about the corresponding body organ and the other parts of the device have also been implanted in the patient, into the injection port 19 by means of a syringe, whose needle has pierced the skin of the patient and the diaphragm 20 of the injection port 19, the desired quantity of sterile water is injected whereby the elastic partition 22 becomes displaced increasing the volume of chamber 24 and decreasing the volume of chamber 23. The filling medium is thereby conducted into the hollow chamber 14, whereby the foamed material body 13 and the wall 11 are extended constricting the passageway cross section of the throughlet opening 6. In this way the throughlet opening 6, and consequently the size of the passageway opening of portion 32 of the gastrointestinal tract, is adjusted to the desired size.

The bulb 21 could instead also comprise a cylinder bore, in which a piston, separating the chambers 23, 24, is disposed, which forms a displaceable partition.

To produce the band 1, the circumferentially closed tube formed by the back segment 9, the connection segments 10 and the wall 11 can initially be produced, in particular in an injection molding process. One end of this tube can herein be developed such that it is closed by a front-side wall 30, the corresponding parts of the closure device 2 also being already molded on, for example the extension 3 with the catch lip 5. Into the open end of the tube a spray nozzle is subsequently introduced up to the closed end of the tube, whose one or several nozzle openings are directed toward the wall 11. While the spray nozzle is slowly pulled out of the tube, a silicone adhesive is sprayed in. The foamed material body is subsequently slid in. To press the foamed material body onto the wall 11, an appropriate wedge can be slid into the hollow chamber 14. Subsequently, or instead, a fluid could also be filled into the hollow chamber 14. The wedge is subsequently pulled out of the hollow chamber or the fluid is drained and the hollow chamber is closed at the other end, for example by means of an end piece comprising a stopper projecting into the hollow chamber, which is adhered on the tube, a part of the closure device 2 also being disposed on the end piece.

Another feasibility for production could comprise introducing the foamed material body 13 initially into the injection-molded tube without first spraying in an adhesive agent. Over its length in the foamed material body through-apertures, spaced apart one from the other, could be provided extending from the hollow chamber 14 to wall 11. Into these through-apertures by means of an injection device, introduced into the hollow chamber and placed into the through-apertures, adhesive agent could sequentially be pressed in, which locally penetrates in each instance into the region between the foamed material ring and the wall 11 and also closes the particular through-apertures in the foamed material body.

A further feasible development form is depicted schematically in FIG. 6. Here a separate back segment 9 is provided, from which extend at both side margins prolongations 28 extending in the direction toward the throughlet opening. Onto a foamed material body 13 a skin, preferably comprised of silicone, is adhered over the entire area covering at least its surface directed toward the throughlet opening 6, the skin preferably also extending over the entire surface, or at least a portion thereof, facing away from the throughlet opening 6, of the foamed material body 13. The segment of this skin in contact on the surface of the foamed material body 13 facing the throughlet opening 6, forms the wall 11 delimiting the inner throughlet opening 6. The foamed material body 13 with the skin adhered thereon is adhered between the prolongations 28.

Differing modifications of the described embodiment examples of the invention are conceivable and possible without going beyond the scope of the invention. For example, the bulb 21 could be omitted and a filling medium, preferably sterile water, could be introduced directly via an injection port 19 into the hollow chamber 14. Instead of the depicted injection port, a pumping device for filling the hollow chamber 14 could also be connected to the connection tubule 15. Such a pumping device could include a reservoir with filling medium, whose volume is variable. If the device is developed as an openable and closable closure, for example as an anal band, the reservoir would need to be changeable in known manner between two sizes of its volume, which correspond to the closed and the open state of the device. Other modifications could relate, for example, to the development of the wall 11, which could also be implemented as a multilayer wall.

The invention claimed is:

1. Device for generating an artificial constriction in the gastrointestinal tract with
    a band (1), which can be placed annularly about a particular portion of the gastrointestinal tract,
    a closure device (2) for connecting the end regions of the band (1), placed annularly about the portion of the gastrointestinal tract, which, in the closed state of the closure device (2), encompasses a throughlet opening (6), the band (1) comprising a hollow chamber (14), which can be filled with a filling medium, extending at least over a large portion of the length of the band (1), and, upon filling the hollow chamber (14), a wall, delimiting the throughlet opening (6), of band (1) extends in the direction toward the axis (7) of the throughlet opening decreasing the size of the throughlet opening, and
    a foamed material body (13) adjoining the surface, facing away from the throughlet opening (6) of the wall (11) delimiting the throughlet opening, and the foamed material body (13) is adhered on the wall (11) at least over a large portion of its area in contact with the wall (11).

2. Device as claimed in claim 1, in which the foamed material body (13) is comprised of silicone foam.

3. Device as claimed in claim 1, in which the wall (11) is comprised of silicone.

4. Device as claimed in claim 1, in which the band (1) on the side remote from the throughlet opening (6) comprises a back segment (9), which has a lower extensibility than the wall (11).

5. Device as claimed in claim 4, in which the hollow chamber (14) on its side remote from the throughlet opening (6) is delimited by the back segment (9).

6. Device as claimed in claim 4, in which the wall (11) and the back segment (9) are formed integrally of one piece of material.

7. Device as claimed in claim 4, in which the wall (11) and the back segment (9) and connection segments (10), optionally provided between the back segment (9) and the wall (11), together form a tube.

8. Device as claimed in claim 4, in which the extensibility of the back segment (9) is less than that of the foamed material body (13).

9. Device as claimed in claim 1, in which the surface (29), facing away from the throughlet opening (6), of the foamed material body (13) delimits the hollow chamber.

10. Device as claimed in claim 1, in which the foamed material body (13) extends over the entire length of the wall (11) delimiting the throughlet opening (6) and is adhered to it over the entire length of this wall (11).

11. Device as claimed in claim 1, in which the device comprises a connection tubule (15) whose inner channel (16) communicates with the hollow chamber (14).

12. Device as claimed in claim 1, in which the filling medium has a higher viscosity than water and is preferably silicone gel.

13. Device as claimed in claim 11, in which the connection tubule (15) is connected to a bulb (21), which comprises a first chamber (23), filled with the filling medium, and a second chamber (24), filled with a pressure medium, both chambers (23, 24) being separated from one another by an elastically extensible or a displaceable partition (22), and the chamber (24) filled with the pressure medium is connected with an injection port (19) or with a pumping device.

14. Device as claimed in claim 1, in which the area, in contact on the wall (11), of the foamed material body (13) is adhered over the entire area on the wall (11).

\* \* \* \* \*